United States Patent
Kasvikis

(10) Patent No.: US 9,492,169 B2
(45) Date of Patent: Nov. 15, 2016

(54) SURGICAL INSTRUMENT FOR JOINING TISSUE

(71) Applicant: Covidien LP, Mansfield, MA (US)

(72) Inventor: Dino Kasvikis, Mansfield, MA (US)

(73) Assignee: Covidien LP, Mansfield, MA (US)

( * ) Notice: Subject to any disclaimer, the term of this patent is extended or adjusted under 35 U.S.C. 154(b) by 198 days.

(21) Appl. No.: 14/282,548

(22) Filed: May 20, 2014

(65) Prior Publication Data

US 2014/0252070 A1    Sep. 11, 2014

Related U.S. Application Data

(60) Continuation of application No. 13/675,479, filed on Nov. 13, 2012, now abandoned, which is a division of application No. 12/698,255, filed on Feb. 2, 2010, now Pat. No. 8,328,061.

(51) Int. Cl.
| | |
|---|---|
| *A61B 17/068* | (2006.01) |
| *A61B 17/072* | (2006.01) |
| *A61B 18/08* | (2006.01) |
| *A61B 17/29* | (2006.01) |

(52) U.S. Cl.
CPC ....... *A61B 17/068* (2013.01); *A61B 17/07207* (2013.01); *A61B 18/085* (2013.01); *A61B 2017/07285* (2013.01); *A61B 2017/2939* (2013.01); *A61B 2017/2946* (2013.01); *A61B 2017/2947* (2013.01)

(58) Field of Classification Search
CPC ........................... A61B 17/068; A61B 18/085
USPC ................................ 227/175.1, 176.1, 180.1
See application file for complete search history.

(56) References Cited

U.S. PATENT DOCUMENTS

| | | | |
|---|---|---|---|
| 3,490,675 A | | 1/1970 | Green et al. |
| 3,589,589 A | | 6/1971 | Akopov |
| 3,638,652 A | | 2/1972 | Kelley |
| 4,379,457 A | | 4/1983 | Gravener et al. |
| 4,383,634 A | | 5/1983 | Green |
| 4,422,567 A | | 12/1983 | Haynes |
| 4,485,817 A | | 12/1984 | Swiggett |
| 4,610,383 A | * | 9/1986 | Rothfuss .......... A61B 17/07207 227/176.1 |
| 4,671,445 A | | 6/1987 | Barker et al. |
| 4,754,909 A | | 7/1988 | Barker et al. |

(Continued)

FOREIGN PATENT DOCUMENTS

| | | |
|---|---|---|
| DE | 3214810 A1 | 11/1983 |
| WO | 03/047436 A2 | 6/2003 |

*Primary Examiner* — Nathaniel Chukwurah

(57) ABSTRACT

A surgical instrument for surgically joining tissue is provided. The surgical instrument includes a handle assembly that includes an actuator member. An end effector is operatively disposed adjacent a distal portion of an elongated shaft of the surgical instrument. The end effector includes a first jaw member pivotably disposed with respect to a second jaw member. The end effector is movable between a first position where the jaw members are spaced from one another, and a second position where the jaw members are in an approximated position. Each of the first and second jaw members includes a respective longitudinal track. An actuation assembly is disposed in mechanical cooperation with the end effector, wherein actuation of the actuation member causes the actuation assembly to translate from a distal portion of the end effector towards a proximal portion of the end effector through the tracks in the first and second jaw members.

16 Claims, 12 Drawing Sheets

(56) References Cited

U.S. PATENT DOCUMENTS

| | | |
|---|---|---|
| 4,784,137 A | 11/1988 | Kulik et al. |
| 4,869,414 A | 9/1989 | Green et al. |
| 4,991,764 A | 2/1991 | Mericle |
| 5,040,715 A | 8/1991 | Green et al. |
| 5,071,052 A | 12/1991 | Rodak et al. |
| 5,071,430 A | 12/1991 | de Salis et al. |
| 5,197,649 A | 3/1993 | Bessler et al. |
| 5,253,793 A | 10/1993 | Green et al. |
| 5,289,963 A | 3/1994 | McGarry et al. |
| 5,312,023 A | 5/1994 | Green et al. |
| 5,318,221 A | 6/1994 | Green et al. |
| 5,326,013 A | 7/1994 | Green et al. |
| 5,356,064 A | 10/1994 | Green et al. |
| 5,364,001 A | 11/1994 | Bryan |
| 5,364,002 A | 11/1994 | Green et al. |
| 5,379,933 A | 1/1995 | Green et al. |
| 5,392,978 A | 2/1995 | Velez et al. |
| 5,397,046 A | 3/1995 | Savage et al. |
| 5,405,073 A | 4/1995 | Porter |
| 5,411,508 A | 5/1995 | Bessler et al. |
| 5,413,268 A | 5/1995 | Green et al. |
| 5,415,334 A | 5/1995 | Williamson et al. |
| 5,425,745 A | 6/1995 | Green et al. |
| 5,431,322 A | 7/1995 | Green et al. |
| 5,452,836 A | 9/1995 | Huitema et al. |
| 5,456,401 A | 10/1995 | Green et al. |
| 5,465,894 A | 11/1995 | Clark et al. |
| 5,472,132 A | 12/1995 | Savage et al. |
| 5,478,003 A | 12/1995 | Green et al. |
| 5,482,197 A | 1/1996 | Green et al. |
| 5,485,952 A | 1/1996 | Fontayne |
| 5,487,499 A | 1/1996 | Sorrentino et al. |
| 5,497,933 A | 3/1996 | DeFonzo et al. |
| 5,507,426 A | 4/1996 | Young et al. |
| 5,507,773 A | 4/1996 | Huitema et al. |
| 5,554,169 A | 9/1996 | Green et al. |
| 5,560,532 A | 10/1996 | DeFonzo et al. |
| 5,562,682 A | 10/1996 | Oberlin et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,116 A * | 11/1996 | Bolanos ............ A61B 17/07207 227/175.3 |
| 5,577,654 A | 11/1996 | Bishop |
| 5,584,425 A | 12/1996 | Savage et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,607,094 A | 3/1997 | Clark et al. |
| 5,626,587 A | 5/1997 | Bishop et al. |
| 5,630,541 A | 5/1997 | Williamson, IV et al. |
| 5,634,584 A | 6/1997 | Okorocha et al. |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,657,921 A | 8/1997 | Young et al. |
| 5,662,662 A | 9/1997 | Bishop et al. |
| 5,676,674 A | 10/1997 | Bolanos et al. |
| 5,706,998 A | 1/1998 | Plyley et al. |
| 5,709,334 A | 1/1998 | Sorrentino et al. |
| 5,732,871 A | 3/1998 | Clark et al. |
| 5,735,445 A | 4/1998 | Vidal et al. |
| 5,758,814 A | 6/1998 | Gallagher et al. |
| 5,762,256 A | 6/1998 | Mastri et al. |
| 5,779,130 A | 7/1998 | Alesi et al. |
| 5,782,396 A | 7/1998 | Mastri et al. |
| 5,797,537 A | 8/1998 | Oberlin et al. |
| 5,817,109 A | 10/1998 | McGarry et al. |
| 5,820,009 A | 10/1998 | Melling et al. |
| 5,865,361 A | 2/1999 | Milliman et al. |
| 5,871,135 A | 2/1999 | Williamson, IV et al. |
| 5,893,506 A | 4/1999 | Powell |
| 5,894,979 A | 4/1999 | Powell |
| 5,897,562 A | 4/1999 | Bolanos et al. |
| 5,918,791 A | 7/1999 | Sorrentino et al. |
| 5,941,442 A | 8/1999 | Geiste et al. |
| 5,954,259 A | 9/1999 | Viola et al. |
| 5,993,464 A | 11/1999 | Knodel |
| 6,010,054 A | 1/2000 | Johnson et al. |
| 6,032,849 A | 3/2000 | Mastri et al. |
| 6,053,390 A | 4/2000 | Green et al. |
| 6,066,144 A | 5/2000 | Wolf et al. |
| 6,079,606 A | 6/2000 | Milliman et al. |
| 6,109,500 A | 8/2000 | Alli et al. |
| 6,126,058 A | 10/2000 | Adams et al. |
| 6,179,195 B1 | 1/2001 | Adams et al. |
| 6,202,914 B1 | 3/2001 | Geiste et al. |
| 6,241,139 B1 | 6/2001 | Milliman et al. |
| 6,241,140 B1 | 6/2001 | Adams et al. |
| 6,264,087 B1 | 7/2001 | Whitman |
| 6,315,184 B1 | 11/2001 | Whitman |
| 6,330,965 B1 | 12/2001 | Milliman et al. |
| 6,348,061 B1 | 2/2002 | Whitman |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,520,971 B1 | 2/2003 | Perry et al. |
| 6,533,157 B1 | 3/2003 | Whitman |
| 6,544,271 B1 | 4/2003 | Adams et al. |
| 6,601,749 B2 | 8/2003 | Sullivan et al. |
| 6,619,529 B2 | 9/2003 | Green et al. |
| 6,629,630 B2 | 10/2003 | Adams |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,230 B2 | 4/2004 | Whitman |
| 6,716,232 B1 | 4/2004 | Vidal et al. |
| 6,716,233 B1 | 4/2004 | Whitman |
| 6,755,338 B2 | 6/2004 | Hahnen et al. |
| 6,773,440 B2 | 8/2004 | Gannoe et al. |
| 6,793,652 B1 | 9/2004 | Whitman et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,877,647 B2 | 4/2005 | Ratcliff et al. |
| 6,953,139 B2 | 10/2005 | Milliman et al. |
| 6,981,941 B2 | 1/2006 | Whitman et al. |
| 6,986,451 B1 | 1/2006 | Mastri et al. |
| 7,011,668 B2 | 3/2006 | Sancoff et al. |
| 7,032,798 B2 | 4/2006 | Whitman et al. |
| 7,032,799 B2 | 4/2006 | Viola et al. |
| 7,037,315 B2 | 5/2006 | Sancoff et al. |
| 7,044,353 B2 | 5/2006 | Mastri et al. |
| 7,077,856 B2 | 7/2006 | Whitman |
| 7,083,629 B2 | 8/2006 | Weller et al. |
| 7,087,071 B2 | 8/2006 | Nicholas et al. |
| 7,097,089 B2 | 8/2006 | Marczyk |
| 7,097,650 B2 | 8/2006 | Weller et al. |
| 7,114,642 B2 | 10/2006 | Whitman |
| 7,128,253 B2 | 10/2006 | Mastri et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,143,924 B2 | 12/2006 | Scirica et al. |
| 7,159,750 B2 | 1/2007 | Racenet et al. |
| 7,172,104 B2 | 2/2007 | Scirica et al. |
| 7,175,638 B2 | 2/2007 | Gannoe et al. |

(56) References Cited

U.S. PATENT DOCUMENTS

| | | |
|---|---|---|
| 7,188,758 B2 | 3/2007 | Viola et al. |
| 7,210,609 B2 | 5/2007 | Leiboff et al. |
| 7,211,094 B2 | 5/2007 | Gannoe et al. |
| 7,214,233 B2 | 5/2007 | Gannoe et al. |
| 7,220,237 B2 | 5/2007 | Gannoe et al. |
| 7,225,963 B2 | 6/2007 | Scirica |
| 7,225,964 B2 | 6/2007 | Mastri et al. |
| 7,229,428 B2 | 6/2007 | Gannoe et al. |
| 7,235,089 B1 | 6/2007 | McGuckin, Jr. |
| 7,238,195 B2 | 7/2007 | Viola |
| 7,258,262 B2 | 8/2007 | Mastri et al. |
| 7,264,625 B1 | 9/2007 | Buncke |
| 7,278,562 B2 | 10/2007 | Mastri et al. |
| 7,288,099 B2 | 10/2007 | Deem et al. |
| 7,288,101 B2 | 10/2007 | Deem et al. |
| 7,296,722 B2 | 11/2007 | Ivanko |
| 7,296,724 B2 | 11/2007 | Green et al. |
| 7,303,107 B2 | 12/2007 | Milliman et al. |
| 7,306,614 B2 | 12/2007 | Weller et al. |
| 7,308,998 B2 | 12/2007 | Mastri et al. |
| 7,326,232 B2 | 2/2008 | Viola et al. |
| 7,334,717 B2 | 2/2008 | Rethy et al. |
| 7,407,075 B2 | 8/2008 | Holsten et al. |
| RE40,514 E | 9/2008 | Mastri et al. |
| 7,424,965 B2 | 9/2008 | Racenet et al. |
| 7,431,189 B2 | 10/2008 | Shelton, IV et al. |
| 7,434,716 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,448,525 B2 | 11/2008 | Shelton, IV et al. |
| 7,455,676 B2 | 11/2008 | Holsten et al. |
| 7,464,846 B2 | 12/2008 | Shelton, IV et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,503,922 B2 | 3/2009 | Deem et al. |
| 7,506,791 B2 | 3/2009 | Omaits et al. |
| 7,510,559 B2 | 3/2009 | Deem et al. |
| 7,537,602 B2 | 5/2009 | Whitman |
| 7,543,729 B2 | 6/2009 | Ivanko |
| 7,543,731 B2 | 6/2009 | Green et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,571,845 B2 | 8/2009 | Viola |
| 7,572,265 B2 | 8/2009 | Stone et al. |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,617,961 B2 * | 11/2009 | Viola ............... A61B 17/07207 227/175.1 |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,658,311 B2 | 2/2010 | Boudreaux |
| 7,665,647 B2 | 2/2010 | Shelton, IV et al. |
| 7,666,194 B2 | 2/2010 | Field et al. |
| 2006/0020273 A1 | 1/2006 | Hatch et al. |
| 2008/0215811 A1 | 9/2008 | Hajji et al. |
| 2009/0272784 A1 * | 11/2009 | Farascioni ....... A61B 17/07207 227/176.1 |

* cited by examiner

SURGICAL INSTRUMENT FOR JOINING TISSUE

CROSS-REFERENCE TO RELATED APPLICATIONS

This application is a continuation of U.S. patent application Ser. No. 13/675,479, filed Nov. 13, 2012, which is a divisional of U.S. patent application Ser. No. 12/698,255, filed Feb. 2, 2010, now U.S. Pat. No. 8,328,061, the entire disclosure of each of which is hereby incorporated by reference.

BACKGROUND

1. Technical Field

This application relates to surgical instruments for joining tissue, and more particularly, to surgical instruments that are pull activated for sequentially applying a plurality of surgical fasteners to body tissue and to electrosurgical instruments that are configured to sever tissue after tissue has been electrosurgically treated.

2. Background of Related Art

Surgical instruments wherein tissue is first grasped or clamped between opposing jaw structure and then joined by surgical fasteners, or other suitable means, are well known in the art. Instruments for this purpose can include two elongated members which are respectively used to capture or clamp tissue. Typically, such surgical instruments include a shaft extending from a handle and/or trigger assembly, an end effector assembly, which includes an anvil assembly and a cartridge assembly for supporting a plurality of surgical fasteners, an approximation mechanism for approximating the anvil and cartridge and anvil assemblies, and an actuation assembly for ejecting the surgical fasteners from the cartridge assembly. In some instances, the surgical instrument may be adapted to connect to a loading unit (e.g., disposable loading unit) that includes an end effector assembly, which includes an anvil assembly and a cartridge assembly for supporting a plurality of surgical fasteners. Typically, the actuation assembly is operatively coupled to a sled, cam or wedge in operative mechanical communication with the cartridge assembly. During a firing sequence of the surgical instruments, the sled is translated into contact with a pusher associated with a surgical fastener causing the surgical fastener to eject from the cartridge assembly and into the anvil assembly such that a surgical fastener line may be formed within tissue.

Electrosurgical instruments (e.g., electrosurgical forceps) are well known in the medical arts and can include a handle, a shaft and an end effector assembly, which includes jaw members operatively coupled to a distal end of the shaft, that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue. The electrosurgical forceps may include a knife blade or cutter which may be configured to translate within a knife channel or slot operatively associated with one or both of the jaw members such that after the tissue has been electrosurgically treated (e.g., sealed), tissue may be effectively severed.

In some instances, it may prove advantageous to bend or articulate the shaft of the surgical instruments (e.g., during a lower anterior resection "LAR" procedure) and/or the electrosurgical forceps (e.g., during an electrosurgical tissue sealing procedure). When the shaft of the surgical instruments is bent or articulated, there may exist practical challenges associated with a translation force required to translate the sled along the shaft during the firing sequence. Likewise, when the shaft of the electrosurgical forceps is bent or articulated, there may exist practical challenges associated with a translation force required to translate the knife blade within the knife slot after tissue has been electrosurgically treated. When the shaft of the surgical fastener applying instrument is articulated, a force is required to close the anvil assembly and cartridge assembly onto tissue, translate a knife and/or fire or deploy the surgical fastener.

SUMMARY

According to an aspect of the present disclosure, a surgical instrument configured to surgically join tissue is provided. The surgical instrument includes a handle assembly with an actuation member. The surgical instrument includes an elongated portion that extends distally from the handle assembly and defines a longitudinal axis. An end effector is operatively disposed adjacent a distal portion of the elongated portion. The end effector includes a first jaw member pivotably disposed with respect to a second jaw member. The end effector is movable between a first position where the jaw members are spaced from one another, and a second position where the jaw members are in an approximated position. Each of the first and second jaw members includes a respective longitudinal track. An actuation assembly is disposed in mechanical cooperation with the end effector, wherein actuation of the actuation member causes the actuation assembly to translate from a distal portion of the end effector towards a proximal portion of the end effector through the tracks in the first and second jaw members.

The instrument may have an end effector with a cartridge assembly and an anvil assembly. In certain embodiments, the proximal movement of the actuation assembly causes staples to be ejected from the cartridge assembly toward the anvil. The actuation assembly can have cam with a knife, the knife including a proximal edge configured to sever tissue.

A top and a bottom of the cam forms an I-beam shape in certain embodiments. The top and bottom portions of the cam are receivable in tracks in the first jaw member and second jaw member. The end effector can have a cam pin and a cam slot for approximating the first and second jaw members. The distal portion of the second jaw member is configured to house at least a portion of the actuation assembly prior to actuation of the actuation member.

In certain embodiments, the instrument includes an actuation cable in mechanical cooperation with the actuation assembly and with the actuation member. An approximation member can be provided in cooperation with the handle assembly for causing distal translation of an approximation assembly which causes the end effector to move toward the second position.

In certain preferred embodiments, the end effector articulates with respect to the longitudinal axis of the instrument. The end effector may form part of a loading unit that can be removable and replaceable.

In certain embodiments, at least one of the jaw members is pivotable about a pivot point. The surgical instrument can be configured for use in minimally invasive or laparoscopic surgery.

According to an aspect of the present disclosure a loading unit configured for use with a surgical instrument is provided. The loading unit includes a proximal end that is configured to connect to a distal end of the surgical instrument. A distal end includes an end effector having a first jaw member pivotably disposed with respect to a second jaw member. The end effector is movable between a first position where the jaw members are spaced from one another, and a second position where the jaw members are in an approximated position. Each of the first and second jaw members includes a respective longitudinal track. An actuation assembly is disposed in mechanical cooperation with the end effector, wherein actuation of the actuation member causes the actuation assembly to translate from a distal portion of the end effector towards a proximal portion of the end effector through the tracks in the first and second jaw members.

According to another aspect of the present disclosure a surgical stapling instrument is provided. The surgical stapling instrument includes a handle assembly having an actuator member. An elongated shaft extends distally from the handle assembly and defines a longitudinal axis. An end effector is operably disposed at a distal end of the shaft and has a first jaw member with a first distal, free end and a second jaw member with a second distal, free end. One or both of the first jaw member and second jaw member is pivotably movable about a pivot portion at a proximal portion of the jaw members. An actuation head at the first distal, free end of the first jaw member is connected to a flexible actuation member. In one particular embodiment, the first jaw member is a surgical stapling cartridge. A locking feature is operably disposed at the first distal free end of the first jaw member and is configured to maintain the first and second jaw members in a substantially fixed position.

A surgical instrument according to the present disclosure can have a second jaw member which is an anvil assembly.

Proximal movement of the actuation head causes staples to be ejected from the cartridge assembly towards the anvil assembly. The actuation head can include a knife with a proximal edge configured to sever tissue.

In certain embodiments, a top and bottom portion of the actuation head forms an "I" beam configuration, such that the top and bottom portions of the actuation head are receivable within respective tracks associated with the first and second jaw members.

A cam slot and cam pin configuration, in certain embodiments, is operably associated with the end effector and configured to facilitate remote approximation of the first and second jaw members.

The cam slot can be disposed in parallel relation with respect to a proximal end of at least one of the jaw members. The first distal, free end of the first jaw member may be configured to house at least a portion of the actuation head prior to actuation of the actuator member. An approximation member disposed in mechanical cooperation with the handle assembly, wherein actuation of the approximation member causes distal translation of an approximation assembly which causes the end effector to move towards its second position.

The end effector defines a second longitudinal axis and the end effector is desirably movable between a parallel position where the first longitudinal axis is substantially parallel to the second longitudinal axis and an offset position where the first longitudinal axis and the second longitudinal axis are offset from each other.

BRIEF DESCRIPTION OF THE DRAWINGS

Various embodiments of the present disclosure are described herein with reference to the drawings wherein.

DETAILED DESCRIPTION

Figure 1A:
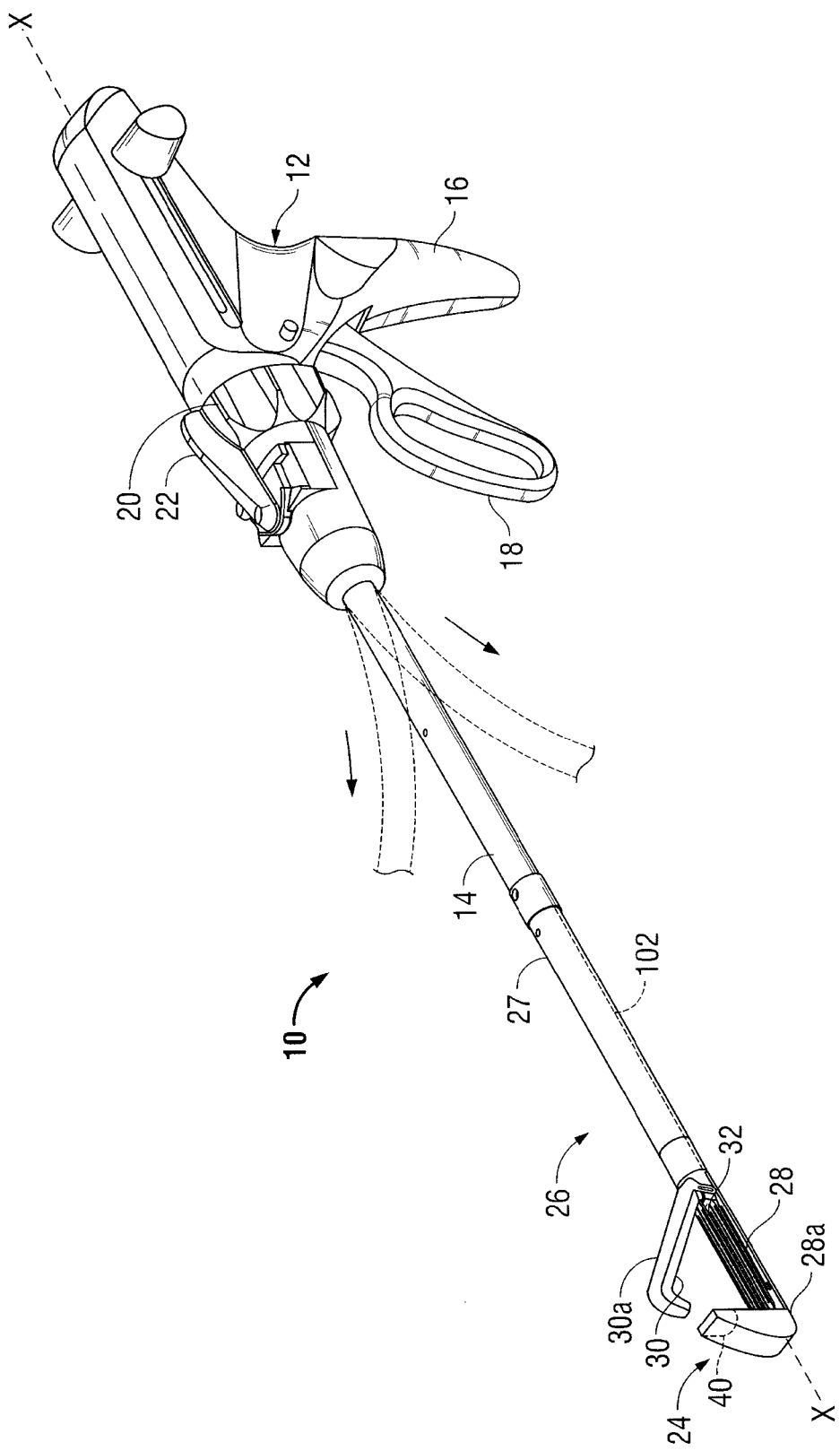
FIG. 1A is a perspective view of a surgical stapling instrument including a loading unit adapted for use with an actuation assembly for sequentially firing a plurality of surgical fasteners in accordance with an embodiment of the present disclosure.

Embodiments of the presently disclosed surgical instrument are described in detail with reference to the drawings, wherein like reference numerals designate similar or identical elements in each of the several views. In the drawings and the description that follows, the term "proximal" refers to the end of the surgical stapling instrument that is closest to the handle assembly, whereas the term "distal" refers to the end of the surgical stapling instrument that is farthest from the handle assembly. As appreciated by one skilled in the art, the depicted surgical stapling instrument fires staples, but it may be adapted to fire any other suitable fastener such as clips and two-part fasteners.

FIG. 1A illustrates one type of surgical stapling instrument that may be employed with an actuation assembly 100 (FIG. 2A-2C) of the present disclosure. Briefly, surgical stapling instrument 10 includes a handle assembly 12 and an elongated body or shaft 14. Shaft 14 defines a longitudinal axis X-X. Shaft 14 may be substantially rigid, or in some instances shaft 14 may flexible and capable of bending, articulating, or pivoting (shown in phantom). Handle assembly 12 includes a stationary handle member 16, and a movable handle member 18. A rotatable member 20 is mounted on the handle assembly 12 to facilitate rotation of elongated body 14 with respect to handle assembly 12. An articulation lever 22 is also mounted on handle assembly 12 to facilitate articulation of an end effector 24. The distal end of instrument 10 may be configured as a loading unit 26 (e.g., a disposable loading unit (DLU) or a single use loading unit (SULU)) that is releasably secured to a distal end of shaft 14. Loading unit 26 includes end effector 24 including a pair of pivotably coupled opposing first and second jaw members 30a and 28a, respectively, including a respective anvil assembly 30 having a plurality of staple forming pockets and cartridge assembly 28 housing a plurality of surgical staples. The first jaw member and cartridge assembly has a first distal, free end and the second jaw member has a second distal, free end. The jaw members are pivotably movable about a pivot portion at a proximal portion of the jaw members. In embodiments, one or both of the cartridge assembly 28 and anvil assembly 30 may be configured to conduct electrosurgical energy.

For a more detailed description of the operation of surgical stapling instrument 10 reference is made to commonly-assigned U.S. Pat. No. 5,865,361 to Milliman et al. and U.S. Pat. No. 5,762,256 to Mastri et al., which are each incorporated herein by reference in their entirety.

Figure 1B:
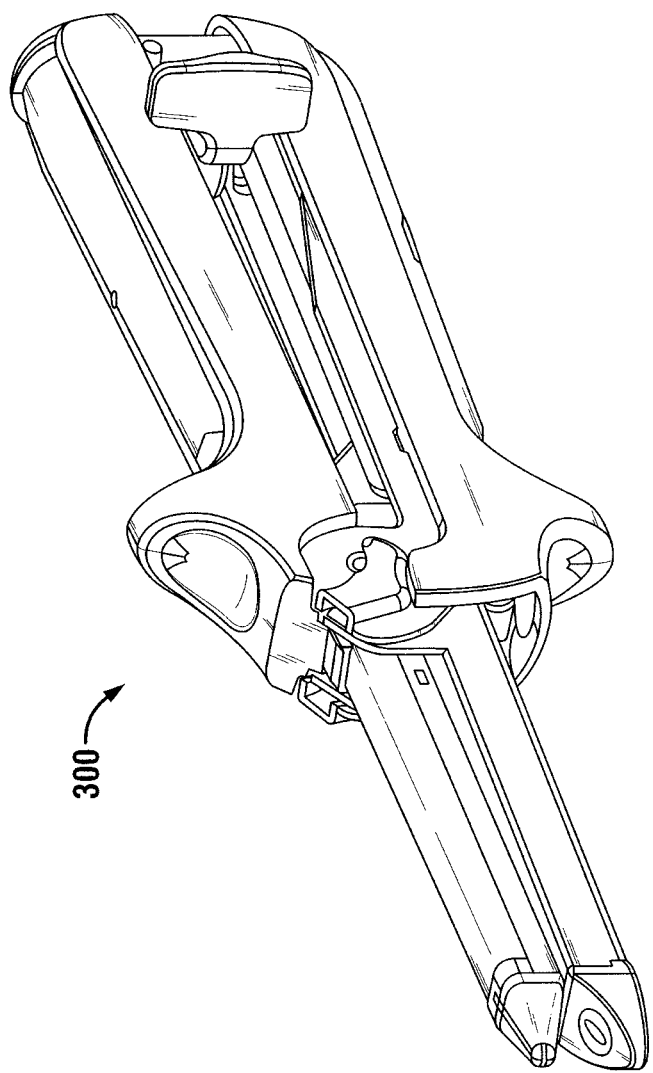
FIG. 1B is a perspective view of an open surgical stapling instrument intended for use with an actuation assembly for sequentially firing a plurality of surgical fasteners in accordance with another embodiment of the present disclosure.

Actuation assembly 100 may be adapted for use with an open surgical stapling instrument 300 (FIG. 1B) that is configured for use during an open gastro-intestinal anastomotic stapling procedure or, for example, any of the surgical fastener-applying apparatus discussed in U.S. Pat. Nos. 6,045,560; 5,964,394; 5,894,979; 5,878,937; 5,915,616; 5,836,503; 5,862,972; 5,817,109; 5,797,538; and 5,782,396, which are each incorporated by reference herein in their entirety.

Figure 1C:
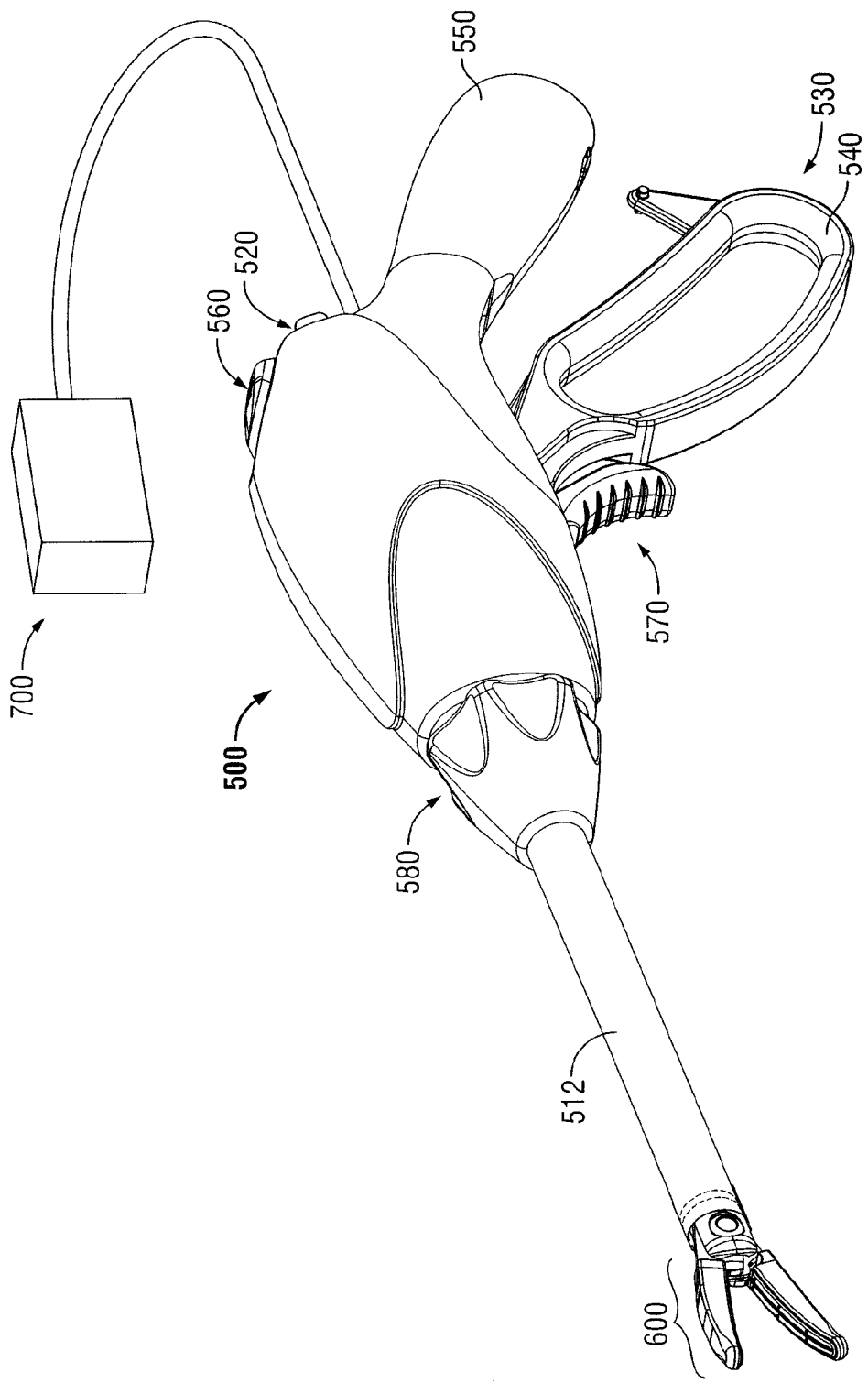
FIG. 1C is a perspective view of an endoscopic electrosurgical forceps intended for use with an actuation assembly in accordance with another embodiment of the present disclosure.

Actuation assembly 100 may be adapted for use with an electrosurgical instrument 500, e.g., an endoscopic electrosurgical forceps 500 (FIG. 1C). Briefly, the electrosurgical instrument 500 can be any suitable type of electrosurgical instrument, including but not limited to electrosurgical instruments that can grasp and/or perform any of the above mentioned electrosurgical procedures. One type of electrosurgical instrument may include an endoscopic electrosurgical forceps 500 as disclosed in United States Patent Publication No. 2007/0173814 entitled "Vessel Sealer and Divider for Large Tissue Structures," which is incorporated by reference herein in its entirety. A brief discussion of endoscopic electrosurgical forceps 500 and components, parts, and members associated therewith is included herein to provide further detail and to aid in the understanding of the present disclosure.

Electrosurgical forceps 500 is shown for use with various electrosurgical procedures (e.g., tissue sealing procedure) and generally includes a housing 520, a handle assembly 530 that includes a movable handle 540 and a fixed handle 550, a rotating assembly 580, a push button assembly 560, a trigger assembly 570, a shaft 512, and an end effector assembly 600, which mutually cooperate to grasp, seal and divide large tubular vessels and large vascular tissues. In embodiments, electrosurgical forceps 500 is adapted to connect to an electrosurgical energy source 700. Although the majority of the figure drawings depict an electrosurgical forceps 500 for use in connection with laparoscopic surgical procedures, the present disclosure may be used for more traditional open surgical procedures or endoscopic procedures.

For the purposes of brevity, the functional and operational features of actuation assembly 100 will be described in terms of use with surgical stapling instrument 10.

Figure 2A:
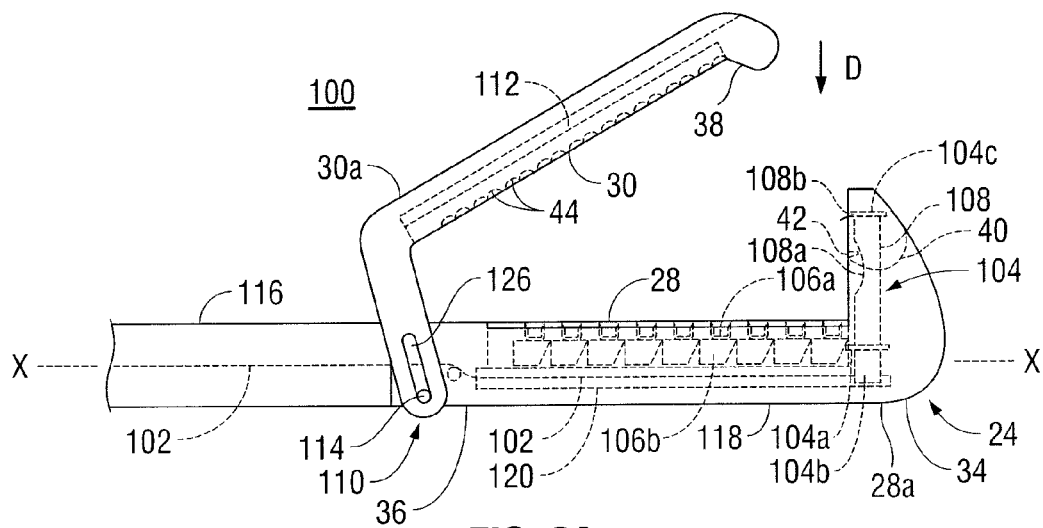
FIGS. 2A-2C are side views in partial phantom of a distal portion of the loading unit depicted in FIG. 1A.
Figure 2B:
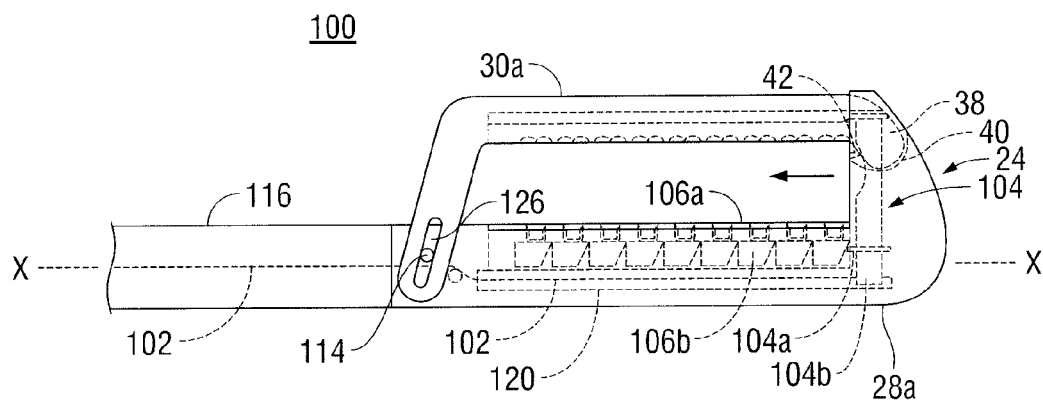
Figure 2C:
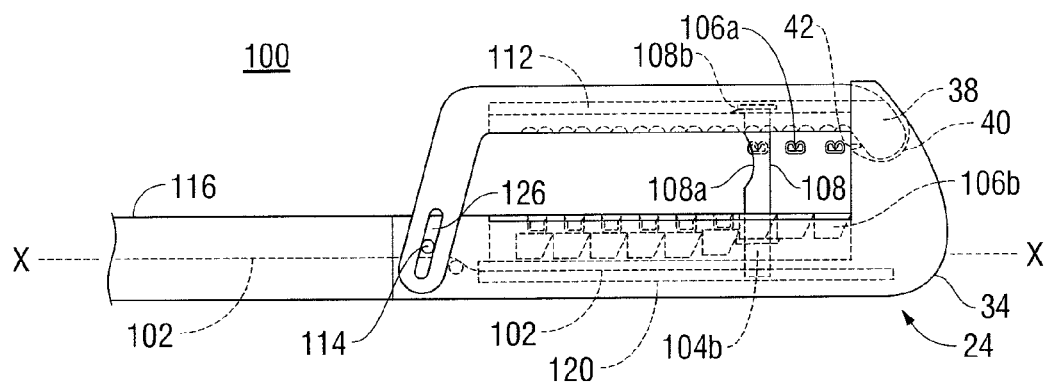

Referring now to FIGS. 2A-2C, and initially with reference to FIG. 2A an embodiment of the actuation assembly 100 for sequentially applying the fasteners of device 10 is shown. In the embodiment illustrated in FIGS. 2A-2C, a proximal end 27 of a loading unit 26 is configured to releasably secure to a distal end of the elongated shaft 14 (see FIG. 1A in combination with FIGS. 3A-3C. The loading unit 26 includes a proximal body and an effector and may be a disposable or replaceable loading unit. Alternatively, a removable cartridge assembly can be used and the cartridge assembly may be replaced after the cartridge assembly is fired.

Actuation assembly 100 may include or be in operative communication with an actuator or trigger member (e.g., movable handle 18) configured such that actuation thereof produces a pulling force that drives a actuation head 104 associated with the actuation assembly 100 proximally causing a plurality of the staples associated with a cartridge assembly 28 to deploy from the cartridge assembly 28. In certain embodiments, the actuation head 104 is disposed at the distal, free end of the first jaw member and cartridge assembly. One such actuator member is disclosed in commonly-assigned U.S. Pat. No. 7,296,724 to Green et al., the entire contents of which is incorporated herein by reference. Loading unit 26, the distal end of elongated shaft 12 and/or any other parts or components associated with device 10 may include any number of gears, screws, pins, cams, links, pulleys, springs, spools, additional conduits, and/or other suitable mechanical/electrical components and/or systems such that the actuation assembly 100 can function in a manner as described herein.

Figure 3A:
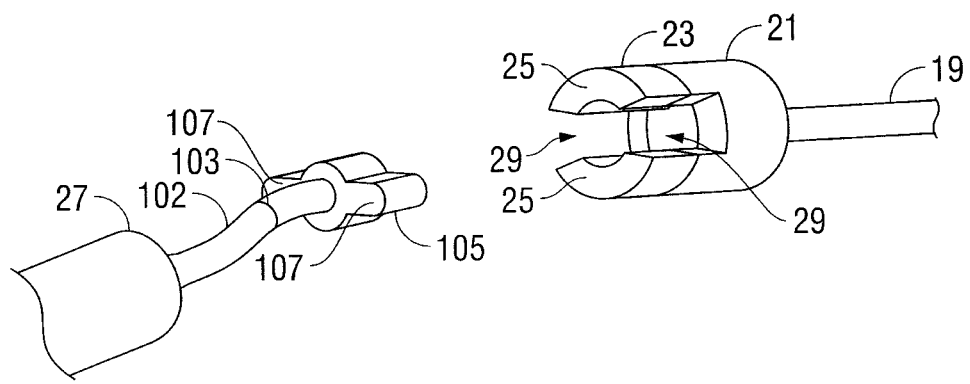
FIG. 3A is a perspective view illustrating a mechanical interface that is utilized to couple a proximal end of the loading unit to the surgical instrument in accordance with an embodiment of the present disclosure.
Figure 3B:
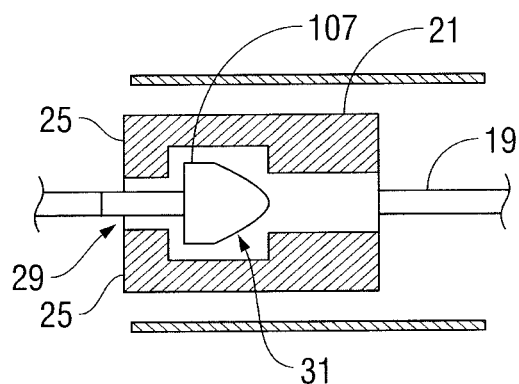
FIG. 3B is a side view of the proximal end of the loading unit coupled to the surgical instrument with the proximal end shown in a locked configuration.
Figure 3C:
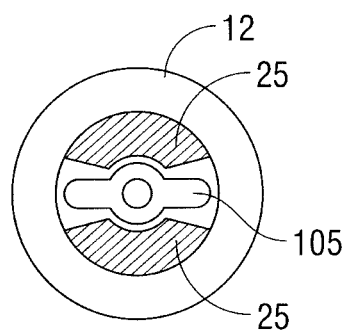
FIG. 3C is a partial cross-sectional view of the proximal end of the loading unit coupled to the surgical instrument with the proximal end shown in an un-locked configuration.

In one particular embodiment, a cable 19 is operably coupled to the movable handle 18 and is configured such that proximal movement of the movable handle 18 causes the cable 19 to move proximally within the shaft 12, which, in turn causes the actuation head 104 to move proximally within the cartridge assembly 28 such that the plurality of the staples associated with a cartridge assembly 28 deploy from the cartridge assembly 28. More particularly, a coupling or locking structure 21 is operably associated with the cable 19 and is configured to matingly and releasably engage a corresponding structure, e.g., a plug 105, associated with an actuation member 102. To this end, locking structure 21 is suitably proportioned to releasably couple to the actuation member 102. More particularly, locking structure 21 includes a generally elongated configuration having a generally circumferential shape, as best seen in FIG. 3A. A proximal end of the locking structure 21 is operably coupled to the cable 19 by one or more suitable coupling methods, e.g., adhesive. A distal end of 23 of the locking structure 21 matingly and releasably secures to the actuation member 102. With this purpose in mind, distal end 23 includes a pair of locking surfaces in the form of a pair of locking tabs 25 that collectively define a pair of lateral slots or notches 29 dimensioned to receive a portion, e.g., plug 105, of the actuation member 102. A cavity 31 of suitable dimension is defined by the locking structure 21 and is disposed between the locking tabs 25 and the proximal end of the locking structure 21. The cavity 31 of the locking structure 21 is dimensioned such that when the plug 105 is positioned within the cavity 31, the plug 105 is movable therein to engage the locking tabs 25. More particularly, after the plug is positioned within the cavity 31 (see FIG. 3C, for example), the loading unit 26 may be rotated such that the plug 105 and locking tabs 25 are in engaged alignment with one another, see FIG. 3B, for example.

Figure 4A:
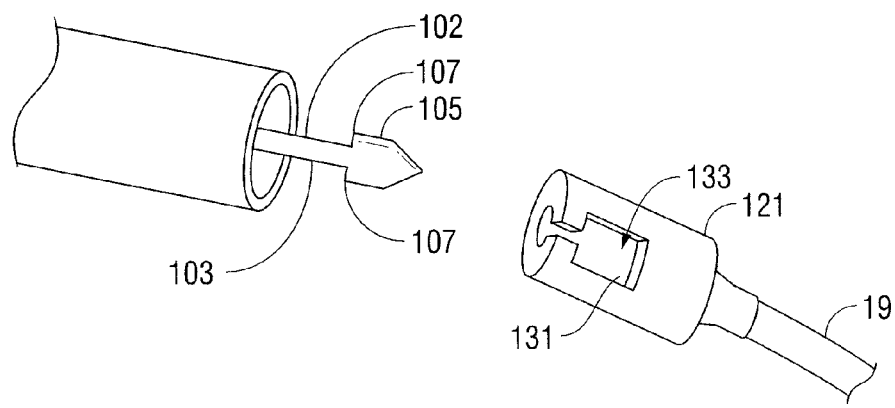
FIG. 4A is a perspective view illustrating a mechanical interface that is utilized to couple a proximal end of the loading unit to the surgical instrument in accordance with an alternate embodiment of the present disclosure.
Figure 4B:
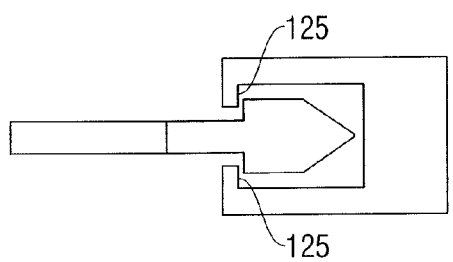
FIG. 4B is a side view of the proximal end of the loading unit depicted in FIG. 4A coupled to the surgical instrument with the proximal end shown in a locked configuration.

With reference to FIGS. 4A and 4B an alternate embodiment of the locking structure is shown designated 121. Locking structure 121 depicted in FIGS. 4A and 4B, is substantially similar to locking structure 21. Locking structure 121 includes a pair of locking surfaces in the form of a pair of locking tabs 125 (FIG. 4B). In FIGS. 4A and 4B, the locking structure 121 includes a single notch 133 that is dimensioned to receive the plug 105 of the actuation member 102 when the loading unit 26 is being attached to the surgical instrument 10, see FIG. 4A, for example. As described above with respect to locking structure 21, once the plug 105 is positioned within the cavity 131, the loading unit 26 may be rotated such that the plug 105 and locking tabs 125 are in engaged alignment with one another, see FIG. 4B, for example.

As can be appreciated by those skilled in the art, other mechanical interface configurations may be utilized to operably couple the cable 19 of the surgical instrument 10 to the actuation member 102 of the loading unit 26.

With reference to FIGS. 1A and 2A, actuation member 102 is shown. Actuation member 102 may be any suitable type of actuation member known in the art including, but not limited to cable, wire, chain, spring (e.g., constant force tension spring such as the one sold by AMETEK® under the trademark NEG'ATOR®) or combination thereof. The actuation member is desirably flexible. In the embodiment illustrated in FIGS. 2A-2C, actuation member 102 is in the form of a flexible cable 102. Cable 102 is configured to stretch, bend and/or articulate when the shaft 14 is in a bent and/or articulated position. Cable 102 may be made from any suitable material. In embodiments, cable 102 may be formed from or coated with a material that is relatively lubricious (e.g., PTFE) such that the coefficient of static and/or kinetic frictions between the cable 102 and other operative components associated with device 10 are kept to a minimum. In an embodiment, cable 102 operatively couples the movable handle 18 to an actuation head 104 that is operatively associated with the end effector 24, to be discussed in more detail below. In the embodiment illustrated in FIGS. 2A-2C, cable 102, or portion thereof, is operatively housed and movable within loading unit 26. Cable 102 extends from a proximal end of loading unit 26 (shown in FIGS. 1A and 3A and 3B) to a distal end 34 of the end effector 24 (FIG. 2A) via an opening (not shown) operatively disposed at a proximal end of end effector 24, cartridge 28, and/or anvil 30. Cable 102 may be configured to translate within a guide, channel or groove operatively disposed within cartridge 18 to facilitate movement of cable 102 within cartridge 18.

In the illustrated embodiments, a proximal end 103 of the cable 102 adjacent the proximal end 27 of the loading unit 26 is configured to couple to a distal end of the shaft of the surgical instrument 10 via one or more of the mechanical interfaces described above, e.g., plug 105 and locking structure 21 or 121. For illustrative purposes, plug 105 is described in terms of use with locking structure 21. As noted above, plug 105 is configured to matingly engage the locking tabs 25 (or in some instances locking tabs 125) of the locking structure 21, see FIG. 3B, for example. A distal end of the plug 105 is operably coupled to the cable 102 by one or more suitable coupling methods, such as, for example, the coupling method utilized to couple the proximal end of the locking structure 21 to the cable 19. Plug 105 includes one or more surfaces that are configured to engage the locking tabs 25. More particularly, plug 105 includes a pair trailing surfaces 107 configured to engage a respective one of the locking tabs 25 (or in some instances locking tabs 125) when the plug 105 is positioned with the cavity 31 and the plug 105 and/or loading unit 26 is rotated from an unlocked position (see FIG. 3C, for example) to the locked position (see FIG. 3B, for example).

A handle assembly with an actuator member that may be used to retract the cable 102 is disclosed in U.S. Pat. No. 5,897,562 to Bolanos et al., the disclosure of which is hereby incorporated by reference herein in its entirety. One or more spools are ratcheted to draw the cable 102 around the one or more spools and retract the cable 102. Detents or pawls are used so that multiple actuations of the trigger handle will wind the cable 102 around the spool.

Actuation assembly 100 includes one or more actuation heads 104 that is operatively associated with the cartridge 28 and disposed at distal end 34 of the end effector 24 (see FIG. 2A, for example). Actuation head 104 is translatable within cartridge 28 from distal end 34 of the end effector 24 to at least a proximal end 36 of the cartridge. To this end, actuation head 104 may include any suitable configuration. In the embodiment illustrated FIGS. 2A-2C, actuation head 104 includes an "I" beam shaped configuration. In addition, a proximal or leading edge 104a (FIG. 2A) of actuation head 104, or portion thereof, is incorporated therein. Leading edge 104a is configured to contact a plurality of pushers 106b operatively disposed within cartridge 28 so that during a firing sequence of the instrument 10 a corresponding plurality of staples 106a are caused to be ejected from the cartridge 28 (FIG. 2C) towards anvil 30. For example, the leading edge 104a may be configured as a wedge or cam. A proximal end of the actuation head 104 operably couples (via adhesive, solder, etc.) to cable 102 (FIG. 2A). A bottom portion 104b of actuation head 104 is translatable within a longitudinal track 120 (e.g., a slot corresponding to the bottom flange of the I-beam) operably associated with the second jaw member 28a and extending substantially along a length of the cartridge 28 (see FIG. 2A, for example). A top portion 104c of actuation head 104 is receivable within a longitudinal track 112 operatively associated with first jaw member 30a and extending substantially along a length thereof. In an embodiment, top portion 104c of actuation head 104 forms a top portion of the "I" beam structure and includes a compression member in the form of a lip or flange 108b that is configured to compress the anvil 30 and cartridge 28 together during the firing sequence.

A knife blade or cutter 108 is operatively connected (via adhesive, solder, etc.) to actuation head 104. Alternatively, knife blade 108 and actuation head 104 may be a unitary structure manufactured by known techniques (e.g., molded, over-molded, etc.) Knife blade 108 is disposed within cartridge 28 at the distal end 34 of the end effector 24. Knife blade 108 includes a leading or proximal edge 108a (FIG. 2A) that is spaced distally relative to the proximal edge 104a of actuation head 104 and includes a generally arcuate or concave configuration. In an alternate embodiment, proximal edge 108a may be flat. In this embodiment, proximal edge 104a of actuation head 104 may be elongated and extend proximally relative to the proximal edge 108a of the knife blade 108. Knife blade 108 is oriented in a substantially perpendicular relation to a longitudinal axis X that extends along the length of device 10 and loading unit 26. Knife blade 108 is translatable from the distal end 34 of the end effector 24 to at least the proximal end 36 of cartridge 28 within a knife channel 32 operatively disposed along a length of cartridge 28 (an example of which is shown in FIG. 1A).

Figure 5:
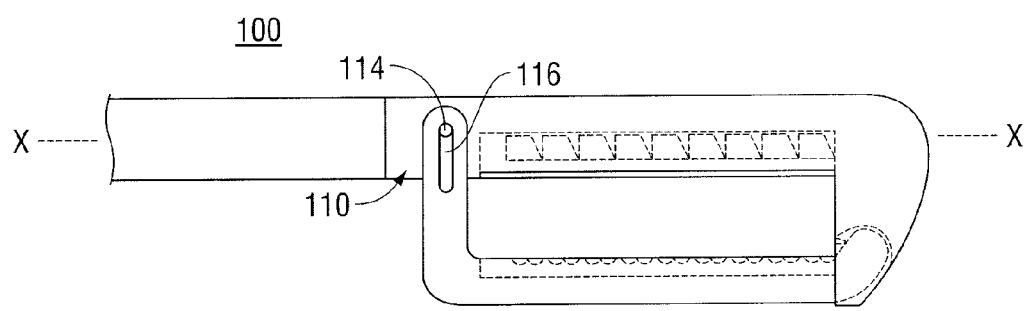
FIG. 5 is a side view in partial phantom of an alternate configuration of an end effector adapted for use with the loading unit depicted in FIGS. 2A-2C.

One or more camming features 110 are operatively disposed on end effector 24. In the embodiment illustrated in FIGS. 2A-2C, camming feature 110 may be employed when manual approximation of the cartridge 28 and anvil 30 is required. That is, the movable handle 18 is not configured to approximate the anvil 30 and cartridge 28 toward each other. To this end, a camming feature 110 is operably positioned on both a right and left side of the end effector 24 (see FIG. 1A in combination with FIGS. 2A-2C). The camming feature 110 on each of the right and left sides of the end effector 24 is identical, thus, and unless otherwise noted, the operative and functional features of each of the camming features 110 will be described in terms of a left camming feature 110. A cam pin 114 is operably associated with the end effector 24 adjacent the cartridge 28 and operatively connects to a cam slot 126 disposed on anvil 30. The cam pin 114 and cam slot 126 may be configured in any suitable configuration. In the embodiment illustrated in FIGS. 2A-2C, the cam slot 126 is obliquely orientated with respect to the X axis and parallel with respect to a proximal portion of the first jaw member 30a, see FIGS. 2B and 2C, for example. In an alternate embodiment, the cam slot 126 is orthogonally oriented with respect to the X axis and parallel with respect to a proximal portion of the first jaw member 30a, as best seen in FIG. 5. In either arrangement, the camming configuration is intended to aid a clinician in approximating the anvil 30 and cartridge 28 toward each other. That is, this camming configuration provides an additional mechanical advantage for overcoming the high forces associated with the clamping down of tissue between the anvil 30 and cartridge 28.

Figure 11:
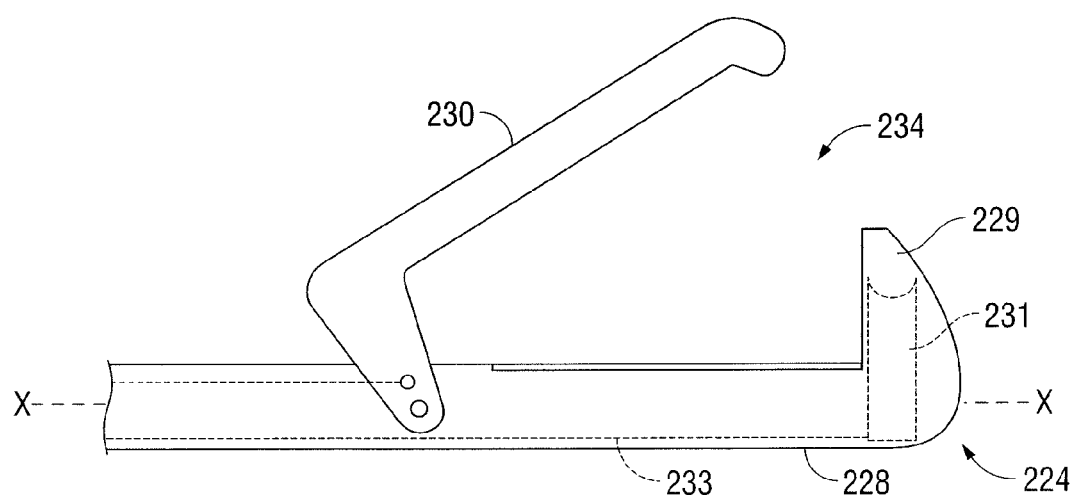
FIG. 11 is a partial cross-sectional view of an end effector for a surgical stapling instrument in accordance with certain aspects of the present disclosure.

In an embodiment, end effector 24 may include one or more types of locking features configured to maintain the anvil 30 and cartridge 28 in an approximated position. The locking feature(s) may be any suitable locking feature(s) known in the art. In certain embodiments, the locking feature is provided at the distal, free end of the cartridge assembly to engage the anvil. For example, in the embodiment illustrated in FIGS. 2A-2C, a distal end 38 of the anvil 30 is configured to engage the distal end 34 of the end effector 24 and/or cartridge 28. More particularly, the distal end 38 of the anvil 30 includes a generally curved or arcuate end configured to selectively and releasably engage an opening or recess 40 associated with the distal end 34 of the end effector 24 (see FIG. 1A in conjunction with either of FIG. 2A or 2C, for example). In the embodiment illustrated in FIGS. 2A-2C, a protrusion 42 is operably disposed within the opening 40 and extends at an angle relative to the axis X toward the distal end 34 of the end effector 24. The protrusion 42 is configured to selectively and releasably engage the arcuate surface 38 of the anvil 30 such that anvil 30 is maintained in a substantially fixed position when the anvil 30 is engaged with the opening 40. To facilitate engagement of the anvil 30 within the opening 40 the protrusion 42 may be biased radially inward. In this instance, the protrusion 42 may be formed from a resilient material, or may be operably associated with a spring (not shown). Other locking features are contemplated herein, such as detents, latches, clips, etc. The anvil 30 has a slot for accommodating the actuation head 104 as the anvil 30 is moved toward the cartridge assembly 28. In certain preferred embodiments, the distal end 234 of the end effector 224 or the jaw opposite the anvil 230 has an inwardly biased (i.e., biased generally in the proximal direction) lock member 231 for securely engaging the anvil 230 (see FIG. 11). The lock member has a recess shaped to securely engage the distal end of the anvil 230 and prevent movement of the anvil 230 or, alternatively, the distal end of the anvil 230 has a recess and the lock member has a protrusion engaged by the recess. The lock member has a first position securing the anvil 230 in place and a second position allowing the anvil to move away from the opposing jaw and allowing the end effector to open and release tissue. In certain preferred embodiments, the lock member is attached to a pusher that extends to handle assembly. The pusher 233 may be attached to a button or other manipulatable member allowing the user of the instrument to release the anvil 230 after the staples have been deployed. Thus, for relatively thick tissue, the second jaw member 228 has a distal end extending transversely to the longitudinal axis, enclosing the gap between the first and second jaw member 228. The first jaw member 30a locks into the second jaw member 228, capturing tissue between the jaws so that relatively thick tissue will not escape the gap between the jaws. The user may release lock, and open the jaws by manipulating the manipulatable member, moving the lock member holding the anvil 230 in place in the closed position. After releasing the lock member, the anvil 230 can be moved to an open position. It is contemplated that the anvil have more than one closed position and that the lock fix the anvil in a first, second, or third position, or more. In such an embodiment, the lock member has more than one feature, such as a recess or protrusion, or the anvil distal end has more than one recess or protrusion.

Operation of actuation assembly 100 is described herein in terms of use with the surgical instrument depicted in FIG. 1A. In operation, tissue is positioned between anvil 30 and cartridge 28 (not explicitly shown). When tissue is properly positioned between the anvil 30 and cartridge 28, a user manually approximates (e.g., in the direction of directional arrow D) the first and second jaw members, 30a and 28a, respectively, toward one another. Curved portion 38 is received into opening 40 where protrusion 42 releasably engages the curved portion 38 (see FIG. 2B, for example). The top portion 104c aligns with the track 112 in first jaw member 130. Subsequently, movable handle 18 is moved through an actuation stroke causing the cable 102 to pull actuation head 104 proximally, which results in knife blade 108 translating proximally within knife channel 32 and bottom portion 104b and top portion 104c of the actuation head 104 translating proximally within respective I-beam tracks 120 and 112. During proximal movement of the actuation head 104, the leading edge 104a, or portion thereof, contacts the plurality of pushers 106b causing the corresponding plurality of staples 106a to eject from the cartridge 28 and form within staple forming pockets 44 associated with the anvil 30 such that at least one staple line is formed in tissue (see FIG. 2C, for example). During proximal movement of the knife blade 108, the proximal edge 108a severs the stapled tissue. Moreover, because cable 102 is flexible and capable of bending and/or articulating, the practical challenges associated with conventional actuation assemblies may be diminished and/or alleviated.

Figure 6:
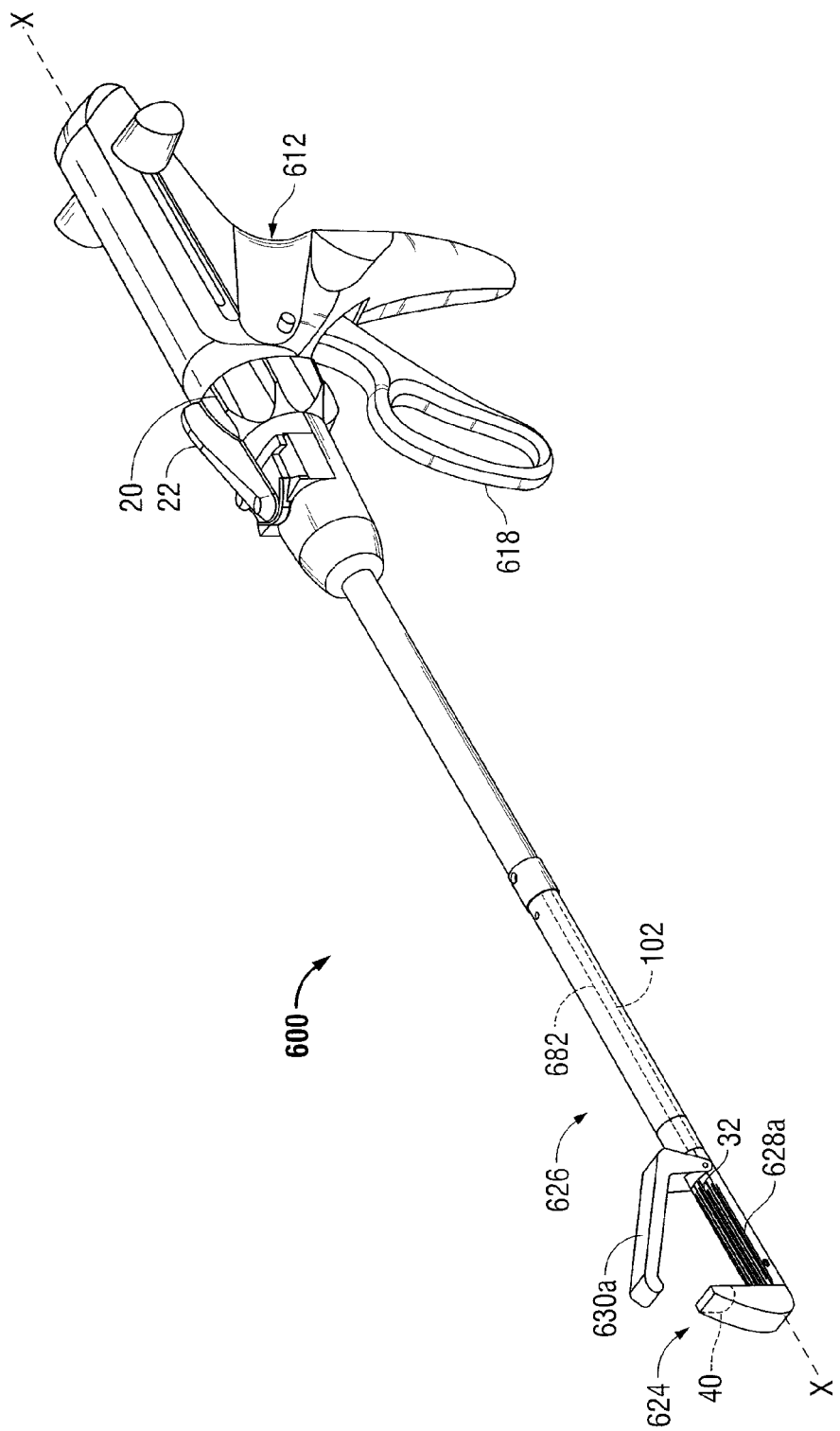
FIG. 6 is a perspective view of a surgical stapling instrument including a loading unit adapted for use with an actuation assembly for sequentially firing a plurality of surgical fasteners in accordance with an embodiment of the present disclosure.
Figure 7A:
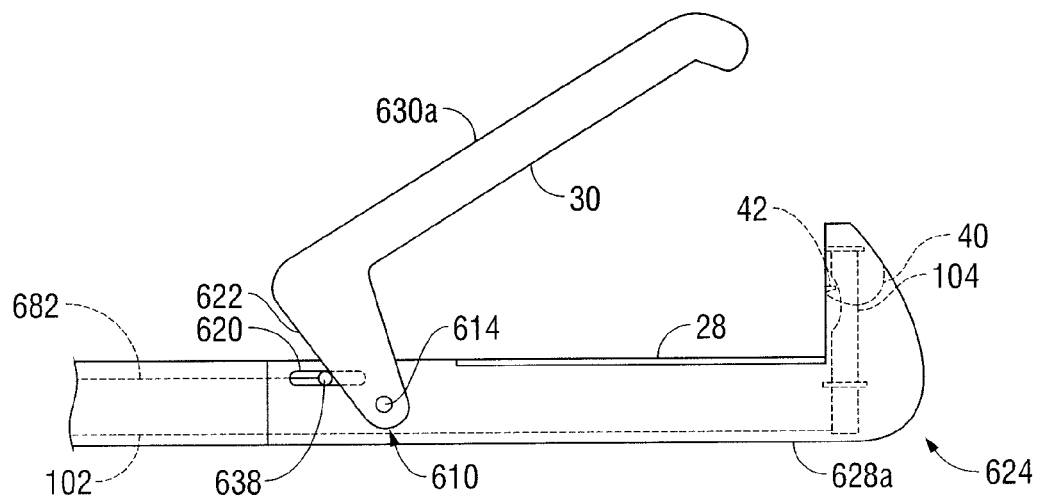
FIGS. 7A-7B are side views in partial phantom of a distal portion of the loading unit depicted in FIG. 4.
Figure 7B:
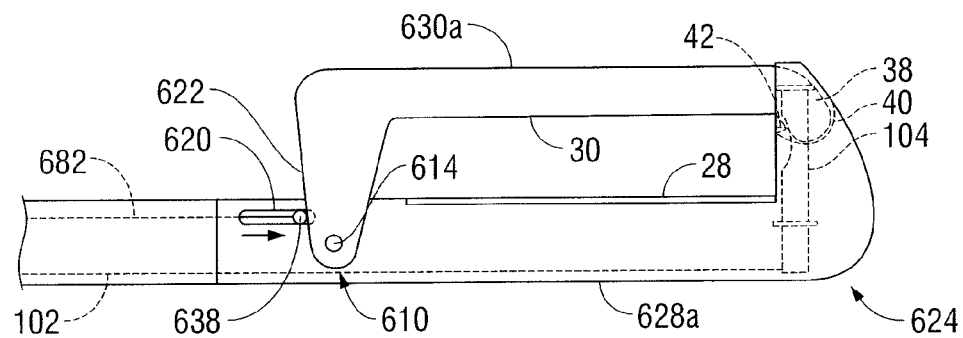

With reference to FIGS. 6-7B, and initially with reference to FIG. 6, a surgical stapling instrument 600 is shown with a loading unit 626 that may be employed with an actuation assembly 100. The operative features of the surgical stapling instrument 600 with loading unit 626 and components associated therewith are similar to surgical stapling instrument 10 with the loading unit 26 described hereinabove. So as not to obscure the present disclosure with redundant information, only the features that are unique to the loading unit 626 and surgical instrument 600 will be described herein.

In the embodiment illustrated in FIGS. 6-7B, a movable handle 618 is configured to approximate a first jaw 630a toward a second jaw 628a. In the embodiment illustrated in FIGS. 6-7B, the first jaw 630a is pivotably coupled to a proximal end of the end effector 624 and biased in a normally open configuration. Additionally, the movable handle 618 is configured to function in a manner as described hereinabove with respect to movable handle 18. That is, movable handle 618 produces a pulling force that drives actuation head 104 associated with the actuation assembly 100 proximally causing a plurality of the staples associated with a cartridge assembly 28 to deploy from the cartridge assembly 28.

With reference to FIGS. 7A and 7B, a camming feature 610 may be employed when the movable handle 618 and is configured to approximate the first jaw 630a toward a second jaw 628a. Camming feature 610 is operably associated with an end effector 624. Camming feature 610 is similar to camming feature 110 described above. More particularly, a pivot pin 614 is operably associated with the end effector 624 adjacent the cartridge 28 and operatively connects to the first jaw 630a. In certain embodiments, the first jaw 630a may include one or more cam slots, e.g., similar to cam slot 116, that is configured to facilitate movement of the first jaw 630a.

A push rod 682 is in mechanical communication with movable handle 618 via a drive mechanism (not shown). One or more cam pins or protuberances 638 are operably disposed at a distal end of the push rod 682 and are in translatable communication with one or more corresponding cam slots 620 extending partially along a length of the end effector 624 adjacent the first jaw member 630 (see FIG. 6 in combination with FIG. 7A). In the embodiment illustrated in FIGS. 6-7B, a pair of protuberances 638 is operably disposed within a corresponding pair of cam slots 620. Each of the protuberances 638 is configured to cause first jaw member 630a to move toward the second jaw member 628a when the protuberance 638 is pushed distally within the cam slot 620 and contacts a portion of the first jaw member 630a.

First jaw member 630a is configured similar to first jaw member 30a. In FIGS. 6-7B, a generally flat (or in certain instances may be generally arcuate) camming surface 622 is located at a proximal end of the first jaw member 630a. Camming surface 622 is in mechanical communication with the protuberance 638. In this instance, the jaw 630a functions as a moment arm created by the distance between 638 and 614, see FIG. 7A for example. More particularly, when the protuberance 638 is pushed distally within the cam slot 620, protuberance 638 contacts a portion of the camming surface 622, which, in turn, effects approximation of the first jaw member 630a toward the second jaw member 628a (FIG. 7B).

In operation, tissue is positioned between anvil 30 and cartridge 28. When tissue is properly positioned between the anvil 30 and cartridge 28, movable handle 618 is moved through an approximation stroke to approximate the first and second jaw members, 630a and 628a, respectively, toward one another. More particularly, when movable handle 618 is moved through the approximation stroke, push rod 682 is forced distally (e.g., via a drive mechanism) pushing protuberances 638 distally within the cam slots 620. During distal translation of the protuberances 638 within the cam slots 620, a portion of the protuberances 638 contacts a portion of the camming surface 622, this, in turn, effects approximation of the first jaw member 630a toward the second jaw member 628a. During the approximation stroke, curved portion 38 is received into opening 40 where protrusion 42 releasably engages the curved portion 38 (FIG. 7B). Subsequently, movable handle 18 may be moved through an actuation stroke causing the actuation member and operative components associated therewith to function in a manner described hereinabove.

Figure 8:
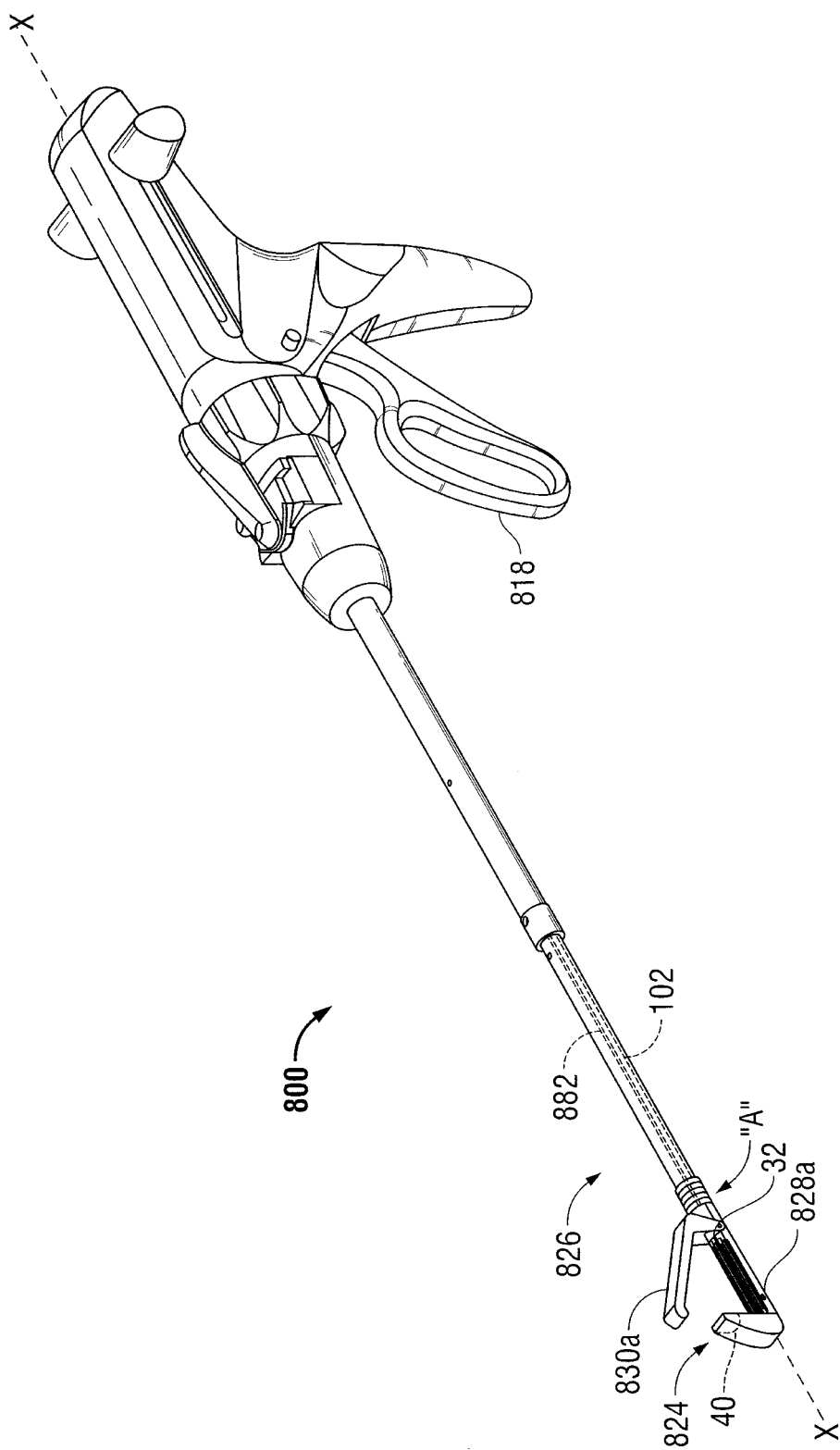
FIG. 8 is a perspective view of a surgical stapling instrument including a loading unit adapted for use with an actuation assembly for sequentially firing a plurality of surgical fasteners in accordance with an embodiment of the present disclosure.
Figure 9A:
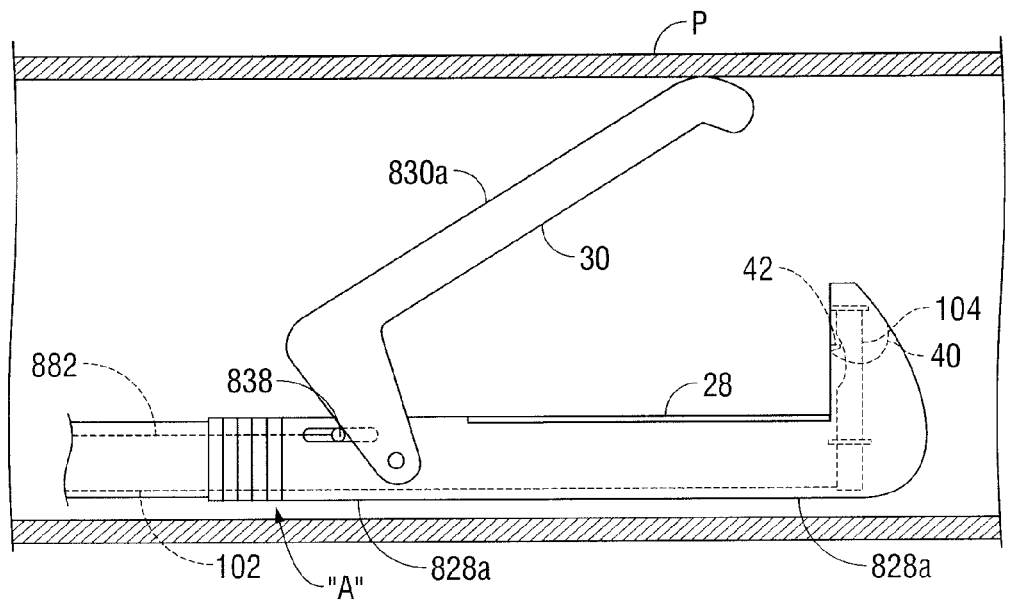
FIG. 9A is a side view in partial phantom of a distal portion of the loading unit depicted in FIG. 6 positioned within an access port and in a non-approximated configuration.
Figure 9B:
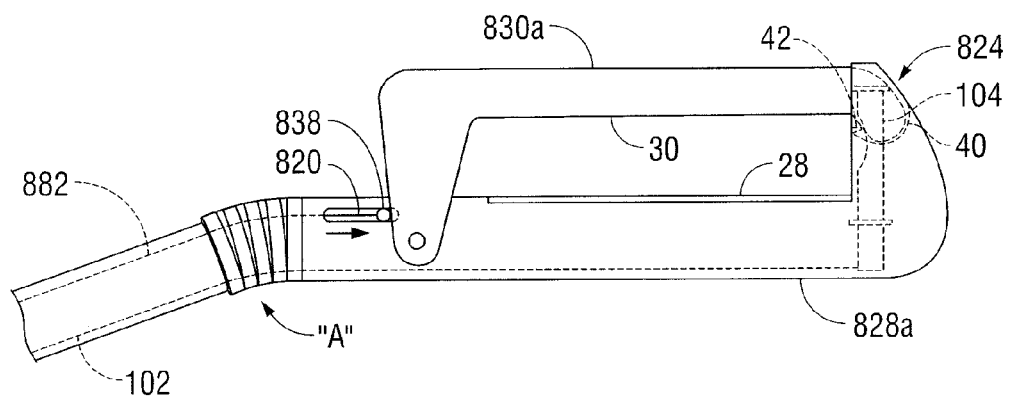
FIG. 9B is a side view in partial phantom of the distal portion of the tool assembly depicted in FIG. 6.

With reference to FIGS. 8-9B, and initially with reference to FIG. 8, a surgical stapling instrument 800 is shown with a loading unit 826 that may be employed with an actuation assembly 100. The operative features of the surgical stapling instrument 800 with loading unit 826 and components associated therewith are similar to the surgical stapling instrument 600 with loading unit 626 described hereinabove. So as not to obscure the present disclosure with redundant information, only the features that are unique to the loading unit 826 and surgical instrument 800 will be described herein.

In the embodiment illustrated in FIGS. 8-9B, the loading unit 826 and/or a surgical stapling instrument 800 are configured for use with a laparoscopic surgical procedure. That is, an end effector 824 of the loading unit 826 is configured for insertion into an access port "P," see FIG. 9A, for example. Surgical port "P" may be a commonly-used trocar assembly and will not be described in further detail.

In the embodiment illustrated in FIGS. 8-9B, loading unit 826 includes an articulation element "A." Loading units that include an articulation element "A" are common in the art. One type of articulation element "A" that may be employed with the loading unit 826 is disclosed in commonly-assigned U.S. Pat. No. 5,865,361 to Milliman et al., the contents of which having been previously incorporated by reference in its entirety.

In FIGS. 8-9B, the loading unit 826 has a push rod 882. More particularly, the push rod 882 is flexible and confined and supported in the elongated shaft so that it (the push rod 882) will not buckle during translation within the elongated shaft. Thus, in the instance where the end effector 824 is in an articulated position (see FIG. 9A, for example), the push rod 882 flexes or bends to the contour of the articulated element "A" and/or the end effector 824. The operative components associated with the push rod 882 are similar to push rod 682 described above. More particularly, push rod 882 is in mechanical communication with a movable handle 818 via a drive mechanism (not shown). A pair of cam pins or protuberances 838 is operably disposed at a distal end of the push rod 882 and is in translatable communication with a corresponding pair of cam slots 820 extending partially along a length of the end effector 824 adjacent the first jaw member 830a (FIG. 9A). Each of the protuberances 838 is configured to cause first jaw member 830a to move toward the second jaw member 828a when the protuberance 838 is pushed distally within the cam slot 820 and contacts a portion of the first jaw member 830a.

In operation, an incision is made in tissue of a patient. An access port "P" is inserted into the incision. Thereafter, the end effector 824 may be inserted into and through the access port "P" (see FIG. 9A, for example). Tissue is positioned between anvil 30 and cartridge 28. When tissue is properly positioned between the anvil 30 and cartridge 28, movable handle 818 is moved through an approximation stroke to approximate the first and second jaw members, 830a and 828a, respectively, toward one another. Curved portion 38 is received into opening 40 where protrusion 42 releasably engages the curved portion 38 (FIG. 9B). Subsequently, movable handle 18 may be moved through an actuation stroke causing the actuation member and operative components associated therewith to function in a manner described hereinabove.

Figure 10:
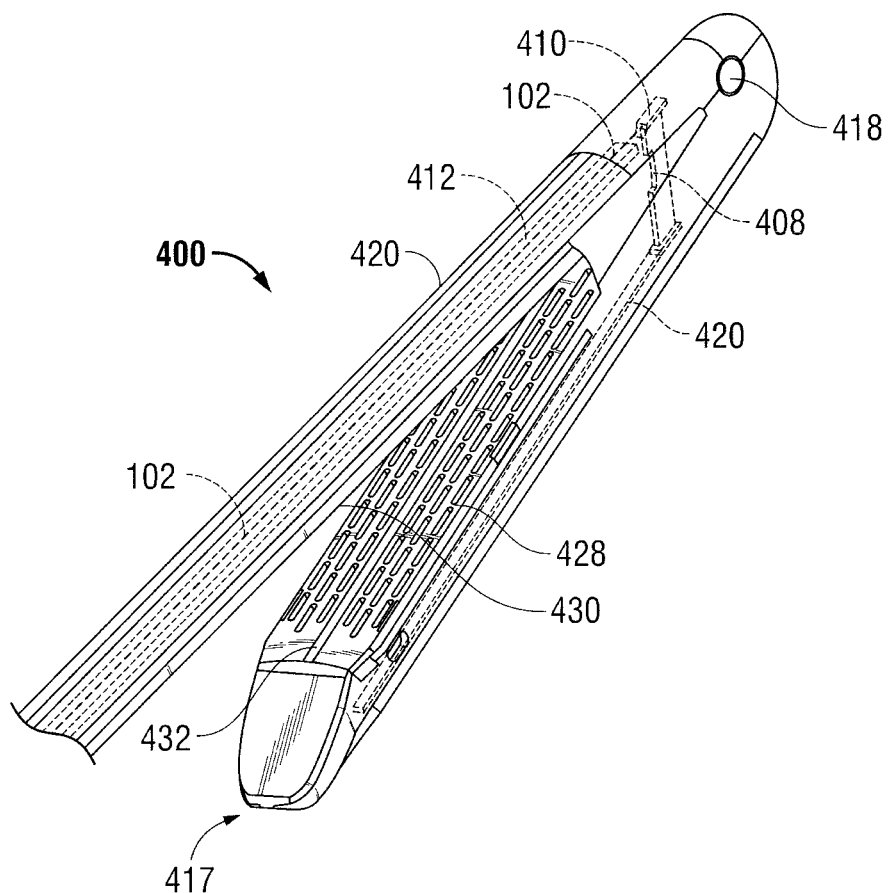
FIG. 10 is a perspective view of a distal portion of a surgical stapling instrument in accordance with an embodiment of the present disclosure.

From the foregoing and with reference to the various figures, those skilled in the art will appreciate that certain modifications can also be made to the present disclosure without departing from the scope of the same. For example, in an embodiment, actuation assembly 400 may be configured for use with a end effector 417 that is configured to pivot about a point 418 at a distal end thereof (see FIG. 10, for example). In the embodiment illustrated in FIG. 8, the actuation assembly 400 may be configured to operate in a manner as previously described herein with reference to actuation assembly 100. For example, end effector 417 may include a cartridge 428 including a track 420, an anvil assembly 430 including a track 412, a track 432, and all components associated with actuation assembly 100 previously described above. In the embodiment illustrated in FIG. 8, cable 102 may extend within anvil 420 and connect to a top portion 410 of knife blade 408.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical stapling instrument comprising:
   an elongated body having a proximal end and a distal end;
   a cable movable within the elongated body, the cable having a proximal end and a distal end supporting a first coupling;
   a loading unit adapted to be releasably secured to the distal end of the elongated body, the loading unit including an end effector and an actuation member, the actuation member having a proximal end supporting a second coupling; and
   an actuation head supported in a distal end of the end effector, the actuation head being secured to a distal end of the actuation member such that proximal movement of the actuation member effects proximal movement of the actuation head within the end effector;
   wherein the first and second couplings are positioned such that when the loading unit is secured to the distal end of the elongated body, the first coupling is releasably coupled to the second coupling to secure the cable to the actuation member.

2. The surgical stapling instrument of claim 1, wherein the actuation member includes a flexible cable.

3. The surgical stapling instrument of claim 2, wherein the loading unit includes a proximal body portion, the end effector being supported to articulate in relation to the proximal body portion.

4. The surgical stapling instrument of claim 2, wherein the first coupling includes a locking structure defining a slot and the second coupling includes a plug which is received in the slot.

5. The surgical stapling instrument of claim 4, wherein the locking structure defines locking tabs and the plug is configured to be rotated within the slot into engagement with the locking tabs to releasably secure the first coupling to the second coupling.

6. The surgical stapling instrument of claim 1, further including a handle assembly including a stationary handle member and a movable handle member, the movable handle member being coupled to the cable.

7. The surgical stapling instrument of claim 1, wherein the end effector includes a first jaw member and a second jaw member, the first jaw member being pivotably coupled to the second jaw member.

8. The surgical stapling instrument of claim 7, wherein the first jaw member supports an anvil assembly and the second jaw member supports a cartridge assembly.

9. The surgical stapling instrument of claim 8, wherein the actuation head has an I-beam configuration.

10. The surgical stapling instrument of claim 9, wherein the actuation head supports a knife blade.

11. The surgical stapling instrument of claim 8, further including a locking feature on a distal end of the end effector configured to retain the anvil assembly and the cartridge assembly in an approximated position.

12. The surgical stapling instrument of claim 11, wherein the end effector defines a recess and the distal end of the anvil assembly defines an arcuate end which is received in the recess when the anvil assembly and the cartridge assembly are in the approximated position.

13. The surgical stapling instrument of claim 12, wherein the locking feature includes a protrusion which is supported on the end effector and positioned to engage the arcuate end of the anvil assembly when the arcuate end is positioned within the recess.

14. The surgical stapling instrument of claim 1, wherein the end effector includes electrosurgical forceps.

15. A surgical stapling instrument comprising:
   an elongated body having a proximal end and a distal end;
   a cable movable within the elongated body, the cable having a proximal end and a distal end supporting a first coupling;
   a loading unit adapted to be releasably secured to the distal end of the elongated body, the loading unit including an end effector and an actuation member, the actuation member having a proximal end supporting a second coupling; and
   an actuation head supported in a distal end of the end effector, the actuation head being secured to a distal end of the actuation member such that proximal movement of the actuation member effects proximal movement of the actuation head within the end effector;
   wherein the first and second couplings are positioned such that when the loading unit is secured to the distal end of the elongated body, the first coupling is releasably coupled to the second coupling to secure the cable to the actuation member,
   wherein the actuation member includes a cable which is coated with a lubricious material.

16. The surgical stapling instrument of claim 15, wherein the lubricious material is PTFE.

* * * * *